United States Patent
Kawamura (10) Patent No.: US 6,452,676 B1
(45) Date of Patent: Sep. 17, 2002

(54) METHOD FOR MEASURING A SCATTERED LIGHT AND METHOD OF URINALYSIS USING THE SAME

(75) Inventor: Tatsurou Kawamura, Kyotanabe (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 09/714,600

(22) Filed: Nov. 17, 2000

(30) Foreign Application Priority Data

Nov. 18, 1999 (JP) .......................................... 11-328786

(51) Int. Cl.$^7$ .............................................. G01N 21/00
(52) U.S. Cl. ...................... 356/338; 356/336; 356/337; 356/138; 250/574
(58) Field of Search ................................ 356/336, 337, 356/338, 339, 340, 341, 342, 343, 73, 138, 244, 246, 39–42; 250/574, 575

(56) References Cited

U.S. PATENT DOCUMENTS

| 4,076,420 A | | 2/1978 | De Maeyer et al. |
| 4,295,199 A | * | 10/1981 | Curry et al. ................. 250/461 |
| 4,906,094 A | * | 3/1990 | Ashida ......................... 356/336 |
| 5,269,937 A | * | 12/1993 | Dollinger et al. ............ 356/368 |
| 5,870,189 A | * | 2/1999 | Uesugi et al. ................ 356/335 |
| 5,940,178 A | | 8/1999 | Barber et al. |
| 6,177,994 B1 | * | 1/2001 | Watson et al. ............... 356/343 |

FOREIGN PATENT DOCUMENTS

| EP | 0 361 770 | 4/1990 |
| EP | 0 455 125 | 11/1991 |

* cited by examiner

Primary Examiner—Frank G. Font
Assistant Examiner—Sang H. Nguyen
(74) Attorney, Agent, or Firm—McDermott, Will & Emery (57) ABSTRACT

The present invention provides a method and an apparatus which eliminate the influences of a scattered light arising due to the pollutants inside and on the surfaces of an optical window, differences in refractive index and light transmittance of a solution to be detected, and the obstruction due to suspending particles and the like to achieve a measurement with high precision and high practicability in the measurement of the scattered light arising. The scattered light propagating within a prescribed angle perpendicularly to the direction of propagation of the light to be propagated through the inside of the solution is measured. Further, the position of the optical axis of the light to be propagated through the inside of the solution and/or the position of the photosensor in the direction of the optical axis are set so that the influence of the scattered light arising at and on the surface of the optical axis is not more than a predetermined value within a practically allowable range.

13 Claims, 5 Drawing Sheets

METHOD FOR MEASURING A SCATTERED LIGHT AND METHOD OF URINALYSIS USING THE SAME

BACKGROUND OF THE INVENTION

The present invention relates to a method and an apparatus for measuring a scattered light arising when a light is propagated through the inside of a liquid sample to be detected such as a urine.

In conventional, when the scattered light of the solution to be detected is measured, there has been adopted a method in which a projected light is focused in the solution to be detected, and the scattered light arisen in the focused region is condensed onto the photo detective area of a photosensor by an integrating sphere or a lens, and detected to trap the scattered light advancing in all directions is trapped as much as possible. Further, by focusing the projected light to generate the scattered light in a smaller region, it is possible to trap the scattered light at a larger solid angle, i.e., range. Consequently, the power of the scattered light reaching the photosensor can be increased, so that the output signal level from the photosensor can also be increased. Further, there is another advantage in that the signal to noise ratio in an electric circuit can be increased.

However, there are present a large number of paths for the scattered light to reach the photosensor, thereby raising the probability of receiving the obstruction due to suspending particles such as bubbles and dust present in the solution to be detected. Further, if the turbidity of the solution to be detected is increased, the proportional relation between the power of the scattered light reached the photosensor through a path with a long optical path length and the turbidity is deteriorated due to a propagation loss. At the same time, the difference in propagation loss due to the difference in optical path length between respective paths is also increased. Then, a calibration curve of the turbidity and the scattered light power to be detected is distorted, resulting in a reduced dynamic range. Further, the scattered light also tends to be affected by the refractive index of the solution to be detected.

Thus, when the measurement is carried out by increasing the trapping rate of the scattered light, the electric signal to noise ratio is improved, but the optical signal to noise ratio, proportional relation, and reproducibility are deteriorated. Especially, the deterioration in optical characteristics is remarkable for the solution to be detected such as a urine, which has a large difference in refractive index, includes a large number of suspending particles such as bubbles and dust, and largely changes in turbidity due to mixing of a reagent, heating, or the like. In such a case, the comprehensive measured characteristics combining the optical and electric characteristics may be deteriorated.

Further, with the foregoing conventional method aimed at trapping the scattered light as much as possible, a cylindrical sample cell or test tube has been generally used for achieving the ease of the arrangement, and the uniformity of the paths for the scattered light. Then, a light has been made incident from the side of the sample cell or test tube to focus the projected light on the central portion. However, such a configuration has presented a problem that the system for condensing the light emitted from the sample cell is enlarged in size and becomes complicated.

Further, as a conventional method of urinalysis, there has been a method in which a test paper impregnated with a reagent, or the like is dipped in a urine, and a color reaction thereof is observed by means of a spectroscope or the like to detect the components of the urine. The test papers herein used have been disadvantageously required to be individually produced according to respective inspection items such as glucose and protein.

It is therefore an object of the present invention to provide a scattered light measuring method and a scattered light measuring apparatus, which reduce the influences of differences in refractive index and optical light transmittance between respective solutions to be detected, for solving the foregoing prior-art problems.

It is another object of the present invention to provide a method for measuring a scattered light, whereby the influences of the pollutants inside and on the surfaces of an optical window are reduced.

It is a further object of the present invention to provide a method of urinalysis which has high reliability, is easy to maintain and control, and has high practical utility.

BRIEF SUMMARY OF THE INVENTION

The present invention relates to a method for measuring a scattered light arising when a light is propagated through an inside of a solution to be detected, comprising the steps of: allowing a light to be incident upon and propagated from a first optical window into the solution to be detected in a sample cell, which has at least the first optical window and a second optical window; and measuring by a photosensor a scattered light propagating in a direction substantially perpendicular to the propagating direction of the light propagating through the inside of the solution to be detected out of a scattered light arising in the solution to be detected from the second optical window. In this method, it is effective that a surface of the second optical window closer to the solution to be detected is located substantially in parallel to an optical axis of the light propagating through the inside of the solution to be detected.

Further, it is effective that a position Y of the optical axis of the light propagating through the inside of the solution to be detected is set such that the power of a scattered light incident upon the photo detective area of the photosensor out of a scattered light arising from, i.e., inside and on the surfaces of, the second optical window is not more than a predetermined value within a practically allowable range.

Still further, it is effective that a position Y of the optical axis and a position Z of the photosensor are set such that the power of the scattered light incident upon the photo detective area of the photosensor out of the scattered light arising from, i.e., inside and on the surfaces of, the first optical window is not more than a predetermined value within a practically allowable range.

On the other hand, it is effective that the position Z of the photosensor is set such that a scattered light arisen in a region closest to the surface of the first optical window, said surface being closer to (in contact with) the solution to be detected, can be measured.

It is also effective that the position Y of the optical axis is set at a position closest to the surface of the second optical window, said surface being closer to (in contact with) the solution to be detected.

Further, it is effective that the light propagating through the inside of the solution to be detected is a linearly polarized light, and that a scattered light propagating in a direction perpendicular to the polarization direction, which is a vibrating direction of a magnetic field of the light, is measured.

Still further, it is effective that the light to be propagated through the inside of the solution to be detected is a substantially parallel light, and the light is made incident such that the light propagates in a direction perpendicular to the surface of the optical window closer to the solution to be detected.

It is effective that the predetermined value is set by defining the power of a scattered light arising inside and on the surfaces of the second optical window from the proportion of the power of the light propagating inside and on the surfaces of the second optical window out of the power of the light to be propagated through the inside of the solution to be detected.

Further, it is also effective that the predetermined value is set by defining the power of a scattered light arising inside and on the surfaces of the first optical window from the proportion of the power of the light propagating in a region within the first optical window, where a scattered light receivable by the photosensor is generated, out of the power of the light to be propagated through the inside of the solution to be detected.

It is effective that the position Y of the optical axis and the position Z of the photosensor are set such that, under the condition that the first and second optical windows contaminated, the power of a scattered light incident upon the photosensor out of the scattered light arisen at both the first and second optical windows is not more than the predetermined value.

Further, it is also effective that the position Y of the optical axis and the position Z of the photosensor are set such that the power of a scattered light to be measured by using a solution to be detected, which has a minimum refractive index and generates substantially no scattered light, is not more than the predetermined value.

Further, the present invention also relates to a method of urinalysis comprising the steps of: opacifying a urine as a solution to be detected by heating and coagulating a protein in the urine, or by mixing therein a reagent for coagulating the protein, measuring a scattered light arising in accordance with the opacity of the urine with the above-mentioned method for measuring a scattered light, and determining the protein concentration in the solution to be detected from the measured value.

Still further, the present invention relates to a scattered light measuring apparatus, which comprises: a rectangular sample cell having at least two adjacent transparent side walls each functioning as optical window and holding a solution to be detected; a light source for projecting a light into the solution to be detected in a direction perpendicular to the surface, which is in contact with the solution to be detected, of a first optical window of the sample cell through the first optical window; a photosensor for detecting a scattered light arising when the light is propagated through the inside of the solution to be detected, and emitted through a second optical window adjacent to the first optical window; and a detecting angle restricting means for restricting the angle of a scattered light incident upon the photosensor within a predetermined angle centering on a direction perpendicular to the propagating direction of the light to be propagated through the inside of the solution to be detected, wherein a scattered light intensity of the solution to be detected is measured by an output signal from the photosensor.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

A method for measuring a scattered light in accordance with the present invention is a method for measuring a scattered light arising in a solution to be detected, i.e. a sample solution, when a light is propagated through the inside of the solution to be detected, and it is characterized by measuring a scattered light propagating in a direction perpendicular to the propagating direction of the light to be propagated through the inside of the solution to be detected out of a whole scattered light by a photosensor.

Herein, although the scattered light in the perpendicular direction is measured in the present invention, in actuality, the whole scattered light does not necessarily propagates in the perpendicular direction. For this reason, the scattered light propagating within a certain angle range with respect to the perpendicular direction may also be measured.

By restricting the detecting angle as described above, the influence of a difference in refractive index between respective solutions to be detected on the scattered light can be reduced, and the influence of the scattered light arisen in a region other than the inside of the solution to be detected is reduced. Accordingly, the scattered light corresponding to the optical characteristics of the solution to be detected itself can be measured with precision.

In the present invention, the surface on the solution side of the second optical window facing the photosensor is preferably located in parallel to the propagating direction of the light to be propagated through the inside of the solution to be detected. Consequently, it is possible to measure a scattered light intensity of the solution to be detected, which has received a further reduced influence of a difference in refractive index between respective solutions to be detected.

In each of the foregoing methods for measuring a scattered light of the present invention, it is preferable that the light to be propagated through the inside of the solution to be detected is a substantially parallel light, and that the light is made incident in a direction perpendicular to the surface of the second optical window in contact with the solution to be detected.

Further, when the light to be propagated through the inside of the solution to be detected is a linearly polarized light, it is preferable to detect the scattered light propagating in a direction perpendicular to the polarization direction, which is a vibrating direction of the magnetic field of the light.

In the method for measuring a scattered light of the present invention, it is preferable that a position Y of the optical axis of the light to be propagated through the inside of the solution to be detected is set such that the power of a scattered light incident upon (projecting onto) the photo detective area of the photosensor out of a scattered light arising inside and on the surfaces of the second optical window facing the photosensor is not more than a predetermined value within a practically allowable range. The position Y of the optical axis is set on the basis of the surface on the solution side of the second optical window facing the photosensor. Consequently, it is possible to reduce the influences of the pollutants and the like inside and on the surfaces of the second optical window facing the photosensor.

In the method for measuring a scattered light of the present invention, it is preferable that the position Y of the optical axis of the light to be propagated through the inside of the solution to be detected and the position Z of the photosensor in the direction of the optical axis are set such that the power of a scattered light incident upon the photo detective area of the photosensor out of the scattered light arising inside and on the surfaces of the first optical window for receiving the light to be propagated through the inside of the solution to be detected is not more than a predetermined value within a practically allowable range.

The position Z of the photosensor in the direction of the optical axis is set on the basis of the surface on the solution side of the first optical window for receiving the light to be propagated through the inside of the solution to be detected. Consequently, it is possible to reduce the influences of the pollutants inside and on the surfaces of the first optical window on the light receiving side.

Herein, it is preferable that the "predetermined value within a practically allowable range" is sufficiently smaller than the minimum value of the power of the scattered light possessed by the solution to be detected when the solution to be detected has the lowest turbidity. Incidentally, although the turbidity differs according to the type, composition, and temperature of the solution to be detected, and the like, it can be appropriately determined according to the group of the solutions to be detected by any those skilled in the art.

Thus, in the present invention, the power of the scattered light incident upon the photo detective area of the photosensor out of the scattered light arising inside and on the surfaces of the first optical window for receiving the light to be propagated through the inside of the solution to be detected, and the scattered light arising inside and on the surfaces of the second optical window facing the photosensor is made sufficiently smaller than the minimum value. Consequently, the threshold values of the positions Y and Z can be determined. Herein, the wording "sufficiently smaller" denotes of such a degree as not to affect the minimum measured value of the turbidity. For example, if it is assumed that the value of not more than $\frac{1}{100}$ of the minimum turbidity exerts no influence thereon, the prescribed value is not more than $\frac{1}{100}$ of the minimum value.

On the other hand, it is preferable to measure a scattered light arisen in a region closest to the surface on the solution side of the first optical window for receiving the light to be propagated through the inside of the solution to be detected ma range of not more than a predetermined value within such a range that the power of the scattered light incident upon the photo detective area of the photosensor out of the scattered light arising in each of the optical windows and on the surface thereof is practically allowable.

Further, it is preferable that the position of the optical axis of the light to be propagated through the inside of the solution to be detected is set at a position closest to the surface on the solution side of the second optical window facing the photosensor within the range of not more than the predetermined value.

With these preferable methods, it is possible to more efficiently reduce the influence of the scattered light arising due to the pollutants at the optical windows and the surfaces thereof.

Specifically, the predetermined value within such a range that the power of the scattered light incident upon the photo detective area of the photosensor out of the scattered light arising in the second optical window facing the photosensor and the surface thereof is practically allowable can be set by defining the power of a scattered light arising inside and on the surfaces of the second optical window from the proportion of the power of the light propagating inside and on the surfaces of the second optical window facing the photosensor out of the power of the light to be propagated through the inside of the solution to be detected.

Further, the predetermined value in such a range that the power of the scattered light incident upon the photo detective area of the photosensor out of the scattered light arising inside and on the surfaces of the first optical window for receiving the light to be propagated through the inside of the solution to be detected is practically allowable can be set by defining the power of a scattered light arising inside and on the surfaces of the first optical window from the proportion of the power of the light propagating in a region within the first optical window, in which a scattered light receivable by the photosensor is generated out of the power of the light to be propagated through the inside of the solution to be detected.

Further, in the present invention, it is preferable that the position Y of the optical axis of the light to be propagated through the inside of the solution to be detected, and the position Z of the photosensor in the direction of the optical axis are set such that, under the condition that the first optical window for receiving the light to be propagated through the inside of the solution to be detected and the second optical window facing the photosensor are contaminated, the power of the scattered light incident upon the photosensor out of the scattered light arisen at both the optical windows is not more than the predetermined value. Consequently, the influence due to the contamination of each optical window can be eliminated to measure the scattered light of the solution to be detected with high precision.

In this case, it is more preferable that the position Y of the optical axis of the light to be propagated through the inside of the solution to be detected and the position Z of the photosensor in the direction of the optical axis are set such that the power of a scattered light to be measured by using a liquid having the lowest refractive index out of solution to be detected, and generating substantially no scattered light is not more than the prescribed value.

The scattered light measuring apparatus of the present invention is for carrying out the foregoing methods for measuring a scattered light, and comprises a rectangular sample cell having at least two adjacent transparent side walls each functioning as optical window for holding a solution to be detected; a light source for projecting a light to be propagated through the inside of the solution to be detected perpendicularly on the solution to be detected through the one optical window of the sample cell; a photosensor for detecting a scattered light arising when the light propagates through the inside of the solution to be detected, and emitted through the other optical window adjacent to the one optical window; and a detecting angle restricting means for restricting the angle of a scattered light incident upon the photosensor within a predetermined angle centering on the direction perpendicular to the direction of propagation of the light to be propagated through the inside of the solution to be detected. Then, it measures the scattered light intensity of the solution to be detected by an output signal from the photosensor.

Herein, the "detecting angle restricting means" denotes a positioning controlling apparatus such as a positioning apparatus comprising a shade column for cutting off an unnecessary light, the light source, and the photosensor, and a computer for controlling the positioning apparatus, or the like.

Further, the foregoing methods for measuring a scattered light can be applied to a method of urinalysis. Therefore, the present invention also provides a method of urinalysis, which comprises: by using a urine opacified by heating and coagulating a protein in the urine, or a urine opacified by mixing therein a reagent for coagulating the protein as a solution to be detected, measuring the scattered light arising in accordance with the opacity of the solution to be detected, and determining the protein concentration in the solution to be detected from the measured value.

Consequently, the high reliability measurement of the concentration of protein in a urine becomes possible, and a simple and accurate urinalysis can be performed.

Below, the method for measuring a scattered light, the scattered light measuring apparatus, and the method of urinalysis in accordance with the present invention will be described in more details with reference to drawings.

Figure 1:
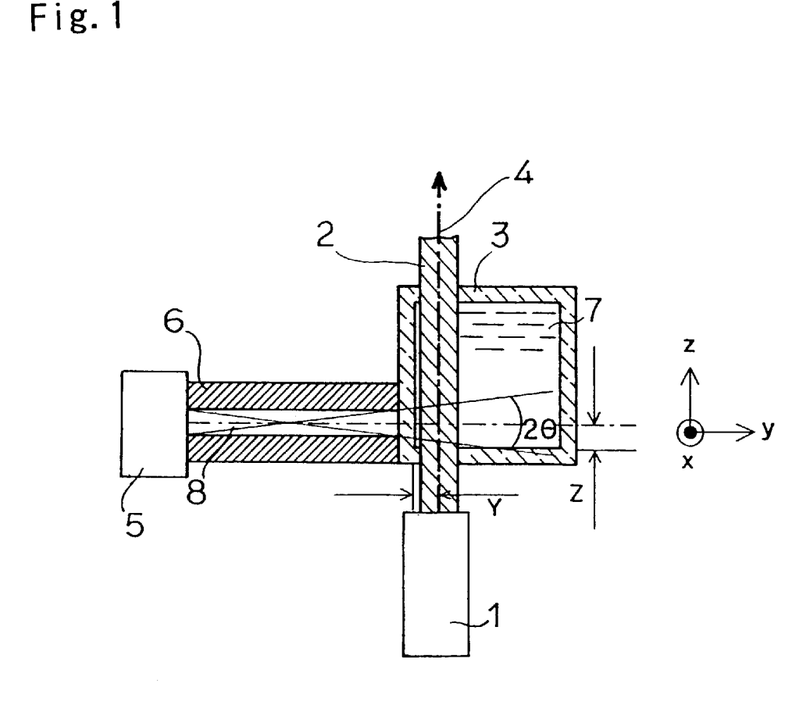
FIG. 1 is a plan view in cross section schematically showing an optical system of a scattered light measuring apparatus in an embodiment of the present invention.
Figure 2:
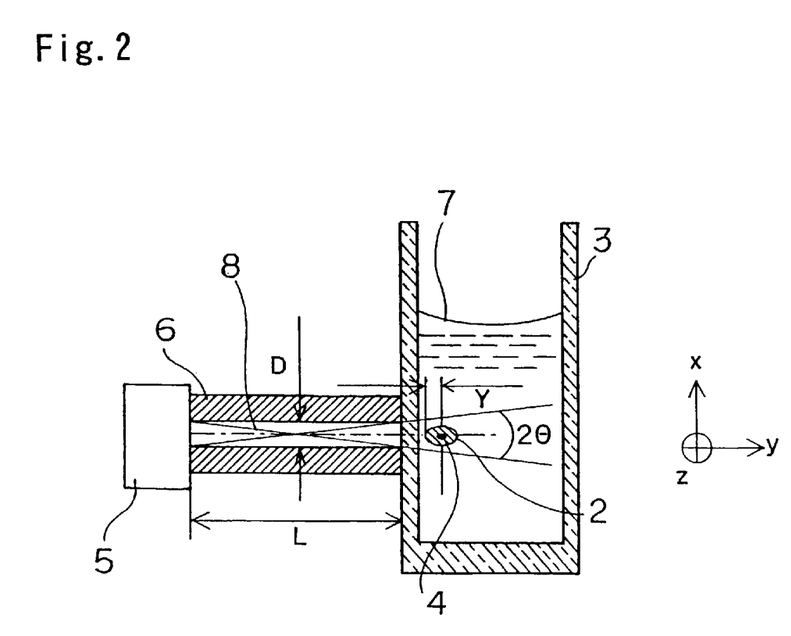
FIG. 2 is a side view in cross section schematically showing the optical system of the same apparatus.

FIGS. 1 and 2 are schematic views of the scattered light measuring apparatus: FIG. 1 is a fragmentary sectional plan view thereof; and FIG. 2 is a fragmentary sectional side view thereof. In FIGS. 1 and 2, a reference numeral 1 denotes a semiconductor laser module which is a light source, and it projects a substantially parallel light 2, i.e., a linearly polarized light with a wavelength of 670 nm and a power of 3.0 mW in the z direction. The substantially parallel light 2 has an elliptic beam form, and an electric field in the x direction. The central axis of the propagation direction, i.e., the optical axis 4 of the substantially parallel light 2 is indicated with a dotted line. Herein, the substantially parallel light 2 is a Gaussian beam which becomes maximum in optical power density on the optical axis 4, and decreases in power density with an increase in distance from the optical axis 4 in accordance with the following formula (1) in the cross section perpendicular to the propagation direction.

$$I(r)=I(0)\times\exp(-2r^2/w_0^2) \quad (1)$$

where, r: distance (m) from the optical axis;

I(r) : power density (W/m$^2$) at a distance of r from the optical axis;

I(0): power density (W/m$^2$) on the optical axis; and $W_0$: distance (m) at which the power density is $1/e^2$ of I(0), in which e is a natural logarithm.

If it is assumed that the beam diameter of the substantially parallel light 2 is the double of $w_0$, the major axis beam diameter (y direction) is 3.0 mm, and the minor axis beam diameter (x direction) is 1.5 mm. In other words, $w_0$ in the y direction is 1.5 mm, and $w_0$ in the x direction is 0.75 mm. The power included within the radius r is obtained by integrating the power density. About 86.5% of the total power of the substantially parallel light 2 is present within the radius $w_0$.

The substantially parallel light 2 is geometrically a parallel light, but, in actuality, it increases in the beam diameter due to the diffraction effect as it propagates. However, there is no harm in substantially considering it as a parallel light for the beam diameter of the foregoing order used in the present invention.

A reference numeral 3 denotes a rectangular-sample cell made of glass, having an opening open upwards, wherein four side walls thereof are transparent optical windows. Respective adjacent optical windows are in perpendicular contact with each other, and the inside dimension of the sample cell 3 is 12 mm per side. The sample cell 3 is capable of making the substantially parallel light 2 incident perpendicularly upon the solution to be detected with the solution held therein, and taking the scattered light out.

A reference numeral 5 denotes a photosensor for detecting the scattered light arisen during propagation of the light through the inside of a solution to be detected 7.

A cylindrical shade column 6 interposed between a second optical window (optical window facing the photosensor 5) through which the scattered light is emitted, and the photosensor 5 is for restricting the detecting angle of the photosensor 5. The cavity serving as an optical path for the scattered light in the shade column 6 has dimensions of a length L and an inside diameter D. The central axis of the shade column 6 lies in the y direction. In other words, the central axis lies in a direction perpendicular to the optical axis direction (z direction) and the electric field direction (x direction). Further, the inner wall of the cavity of the shade column 6 has been subjected to black frosting processing, and hence does not substantially reflects a light. Therefore, consideration from a geometrical viewpoint proves that the detecting angle 2θ is restricted due to the shade column 6 by the following formula (2):

$$2\theta=2\times\tan^{-1}(D/L) \quad (2)$$

Herein, the light receptive portion of the photosensor 5 has an area of not less than the cross sectional area of the cavity portion of the shade column 6. That is, it has an area of not less than the area of the portion surrounded by a circle with a diameter of D. However, the value of 2θ is a virtual detecting angle calculated without considering the difference in refractive index among the air in the cavity portion of the shade column 6, the optical windows of the sample cell 3, and the solution to be detected 7. In other words, the value of 2θ is a detecting angle when it is assumed that the scattered light propagates through a medium having the same refractive index.

Figure 3:
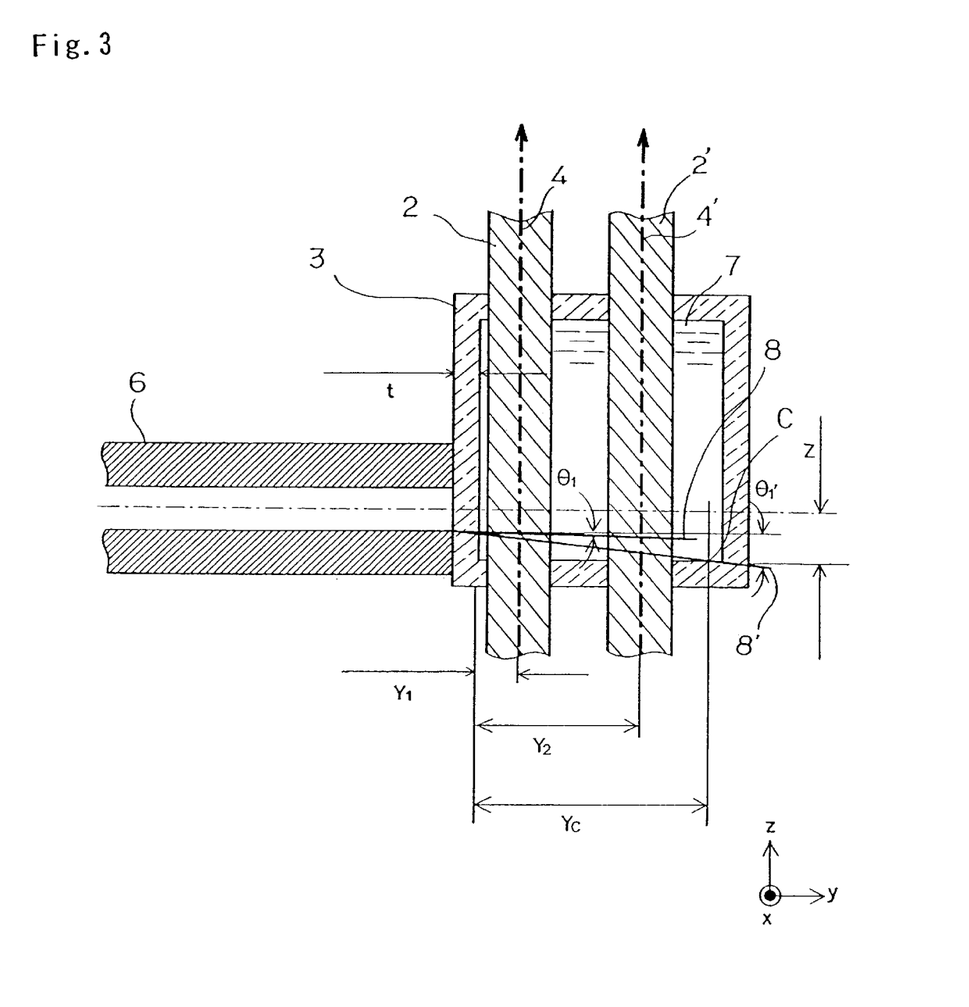
FIG. 3 is an enlarged view showing the essential part of FIG. 1 for illustrating the embodiment of the present invention.

FIG. 3 shows the detecting angle obtained with consideration given to the difference in refractive index among them. In FIG. 3, the thickness of the optical window (second optical window) facing the photosensor 5 of the sample cell 3 is "t". Defining that the refractive indices of air, the optical window of the sample cell 3, and the solution to be detected are $n_a$, $n_g$, and $n_s$, respectively, and as shown in FIG. 3, that the incident angle from the solution to be detected upon the optical window is $\theta_1$, the angle of refraction at the second optical window (angle of incidence upon air) is $\theta_2$, and the angle of refraction in air is $\theta_3$, in accordance with Snell's law of refraction, the formula (3):

$$(\sin \theta_2)/(\sin \theta_1) = n_s/n_g \quad (3)$$

and the formula (4):

$$(\sin \theta_3)/(\sin \theta_2) = n_g/n_a \quad (4)$$

are obtained. It is noted that $\theta_3$ corresponds to $\theta$ in the formula (2).

Further, from the formulae (3) and (4), the following formula (5):

$$\sin \theta_1 = n_a/n_s \times (\sin \theta_3) \approx 1/n_s \times (\sin \theta_3) \quad (5)$$

is introduced. In the formula (5), even if it is assumed that $n_a \approx 1$ when the refractive index of air is $n_a$, there arises no problem from a practical viewpoint. As apparent from the formula (5), if the refractive index $n_s$ of the solution to be detected changes, $2\theta_1$ which is a substantial detecting angle also changes. If it changes, the volume of the region in which the scattered light reaching the photosensor 5 is also changes, thereby affecting the measured value.

Herein, the smaller the detecting angle $2\theta_3$ restricted by the shade column 6 is made, the smaller the amount of changes of the substantial detecting angle $2\theta_1$ due to a difference in refractive index $n_s$ of the solution to be detected can be made. Therefore, by setting the restricted detecting angle $2\theta_3$ small, it is possible to reduce the influence of the refractive index of the solution to be detected.

Then, a description will be given to the relation between the volume change of the region, in which the scattered light to be detected is generated, and the position of the optical axis 4 of the substantially parallel light 2, which is to be propagated through the inside of the solution to be detected, by reference to FIG. 4. Herein, the position Y of the optical axis 4 is represented by the distance "Y" from the surface on the solution side of the second optical window, which faces the photosensor 5 to the optical axis 4.

Figure 4:
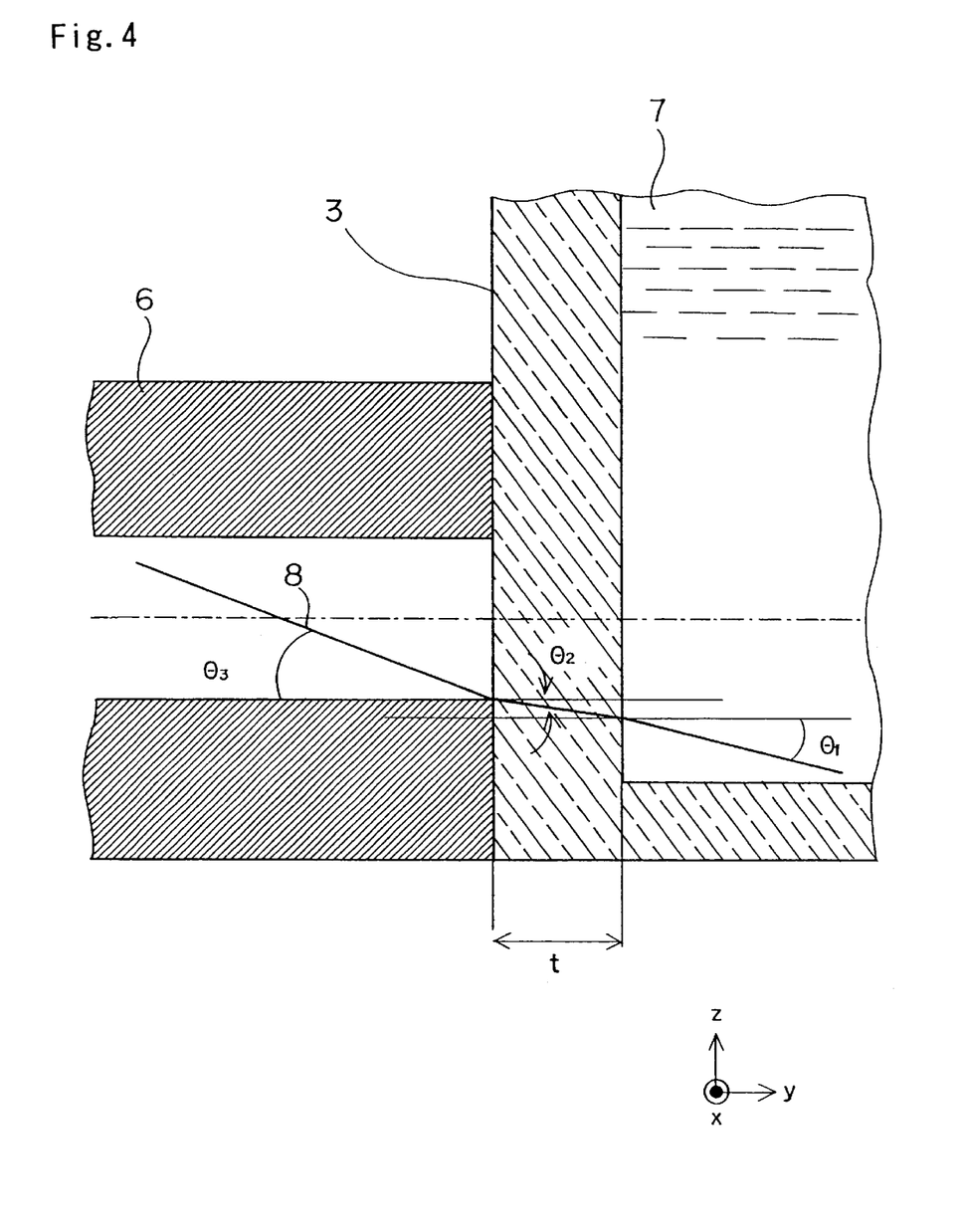
FIG. 4 is an enlarged view showing the essential part of FIG. 1 for illustrating another embodiment of the present invention.

In FIG. 4, the position Y of the optical axis 4 of the substantially parallel light 2 is represented by $Y_1$, and the position Y of the optical axis 4' of a substantially parallel light 2' is represented by $Y_2$ (where $Y_1 < Y_2$). Further, if the $\theta_1$ of a light ray 8 has changed as $\theta_1'$ of a light ray 8' with a change in refractive index of the solution to be detected, the volume of the region in which the scattered light to be detected by the photosensor is generated is larger for the latter case. Then, it is indicated that the volume change based on the change in refractive index becomes larger when the distance Y is large. Therefore, it can be understood that the smaller the distance Y is, the more preferable it is for reducing the influence of a difference in refractive index between the solutions to be detected.

Further, the following consideration can be provided by taking the angle $\theta_3$ restricted by the shade column 6 as a variable. As apparent from the formula (5), the amount of changes in $\theta_3$ with respect to the changes in refractive index $n_s$ of the solution to be detected increases with an increase in $\theta_1$. In other words, an increase in $\theta_1$ increases the amount of changes in $\theta_3$ with respect to the changes in refractive index $n_s$ of the solution to be detected, so that the power of the scattered light reaching the photosensor also largely changes.

On the other hand, when $\theta_1$ is zero, that is, when the scattered light propagates in a direction perpendicular to the optical window, $\theta_3$ becomes zero regardless of the refractive index $n_s$ of the solution to be detected. Accordingly, the power of the scattered light 8 reaching the photosensor does not change.

As described above, by restricting the detecting angle $2\theta_3$ as much as possible by the shade column 6, and reducing the distance Y, it is possible to reduce the influence of the changes in refractive index of the solution to be detected.

Further, since the position Y and angle of the optical axis 4 do not change according to the refractive index of the solution to be detected by making the substantially parallel light 2 incident perpendicularly upon the solution to be detected, it is possible to further reduce the influence of the changes in refractive index.

Below, a description will be given to an example in which the turbidity of the solution to be detected is determined by measuring the scattered light by using the optical system shown in FIGS. 1 and 2.

When the solution to be detected is turbid, as the substantially parallel light 2 propagates, the power thereof attenuates in accordance with the formula (6):

$$P(Z) = P(0) \times \exp(-\tau \times Z) \quad (6)$$

where

Z: distance (m) from the surface on the solution side of the optical window for receiving the substantially parallel light 2 in the z direction;

P(Z): power (W) at a position Z of the substantially parallel light 2;

P(O): power (W) at a position 0 (optical window surface closer to the solution to be detected) of the substantially parallel light 2; and $\tau$: turbidity (1/m).

The scattered light arises in proportion to the power of the substantially parallel light at a generating point. Therefore, when Z is small in the formula (6), that is, when the scattered light arises at the point where the distance Z from the surface on the solution side of the first optical window for receiving the substantially parallel light is short, the power thereof is large. Especially when the turbidity $\tau$ becomes larger, the difference in power between the incident side and the emitting side of the substantially parallel light 2 is magnified, so that the difference in power among scattered lights arising is also magnified. Therefore, the distance Z is desirably reduced as much as possible. The position Z of the photosensor 5 from the reference plane in the optical axis direction can also be represented by the distance Z from the reference plane to the central axis of the shade column 6.

Since the arisen scattered light propagates in all directions except for the direction of the electric field, conventionally, the trap rate of the scattered light has been raised by condensing the scattered light with an integrating sphere or the like. However, since the scattered light has a large number of propagation paths for reaching the photosensor, it is susceptible to the obstruction due to suspending particles such as bubble and dust in the solution to be detected. Further, when the turbidity is high, the linearity of the power of the scattered light reached the photosensor and the turbidity is reduced by a propagation loss, so that the degree of the propagation loss varies according to the difference in optical path length. Accordingly, the dynamic range is reduced. Further, there has occurred another problem that the scattered light also tends to be affected by the refractive index of the solution to be detected.

Thus, with the conventional method, the optical signal to noise ratio, linearity, and reproducibility are reduced. Especially when a solution to be detected, exhibiting a large difference in refractive index, a large influence of suspending particles such as bubbles and dust, and a large turbidity change due to mixing of a reagent, heating, or the like, as with a urine is used, there has presented an especially large problem.

On the other hand, in the present invention, if a laser is used as a light source, the scattered light power itself becomes larger. Accordingly, even if the trap rate of the scattered light is low, the level of an output signal from the photosensor is sufficiently high. Therefore, the reduction in electric signal to noise ratio can be suppressed to a substantially negligible level.

From such viewpoints, according to the present invention, the comprehensive measured characteristics are improved by using a laser as a light source to restrict the path for the scattered light rather than by raising the trap rate of the scattered light. The present invention can be used effectively especially when the difference in turbidity between solutions to be detected is large as with a urine.

Further, if it is set so that the scattered light is emitted at an angle other than the perpendicular direction to the second optical window in restricting the path for the scattered light, the output angle changes according to the refractive index of the solution to be detected, affecting the measured value of the turbidity. As described by using the formulae (3), (4), and (5), according to the present invention, the problem can be solved by restricting the detecting angle within a prescribed angle with respect to the perpendicular direction.

Further, when the sample cell is used repeatedly, a protein component, a scale in running water, and the like may adhere to the optical window. If a light is projected onto the optical window with such a pollutant adhering thereto, the scattered light arises on the optical window surface. Further, the scattered light arises at the optical window due to the striae (uneven-refractive index portion present inside glass) included in the optical window. Incidence of the scattered light arisen from other than the solutions to be detected upon the photosensor exerts an influence upon the measured value of the turbidity.

The influence can be reduced by restricting the detecting angle as described above to prevent the scattered light arisen at the optical window and on the surface thereof from directly reaching the photosensor. That is, by restricting the detecting angle so as to prevent the scattered light from directly reaching the photosensor to restrict the generating region of the incoming scattered light, it is possible to reduce the influences of the striae and contamination of the optical window.

Below, the present invention will be described in more detail by way of concrete examples in which the present invention is applied for a urinalysis.

EXAMPLE 1

Using a urine opacified by heating as a solution to be detected, the scattered light intensity corresponding to the turbidity was measured, to determine the protein concentration from a calibration curve of the measured value and the protein concentration.

In this example, the shade column 6 and the photosensor 5 were integrated in a close contact relation with each other, and moved with respect to the substantially parallel light 2 to change the distances Y and Z. The dimensions of the cavity in the shade column 6 were set such that L=20 mm, and D=2 mm, resulting in that $\theta_3 = \tan^{-}(2/2) \approx 5.71$.

First, there was prepared a sample cell 3 in which the optical windows had been contaminated by adhesion of protein on the inner walls. When a laser light 2 was projected on the optical window of the sample cell 3, the laser light 2 was highly scattered. The thickness t of the optical window of the sample cell 3 was 1.0 mm. A liquid such as pure water, which did not contain a fine particle, and the like, and did not substantially generate a scattered light was introduced into the sample cell 3. Then, the shade column 6 was once fixed at the central portion of the sample cell 3, that is, in the vicinity of a distance Z (=6 mm). Then, the distance Y was gradually reduced until the scattered light arisen inside and on the surfaces of the second optical window facing the photosensor began to enter the photosensor 5. The distance Y at this point where the scattered light began to enter the photosensor 5 was referred to as $Y_{min}$. In this example, it was found that $Y_{min} \approx 2.5$ mm. Then, the distance Y was once fixed at 3 mm, which satisfied $Y_{min} < Y$, and was approximated to $Y_{min}$.

Then, the distance Z was gradually reduced until the scattered light arisen inside and on the surfaces of the first optical window for receiving the substantially parallel light 2 began to enter the photosensor 5. The distance Z at this point where the scattered light began to enter the photosensor 5 was referred to as $Z_{min}$. In this example, it was found that $Z_{min} \approx 1.5$ mm. Then, the distance Z was once fixed at 2.0 mm, which satisfied $Z_{min} < Z$, and was approximated to $Z_{min}$.

In this state, each of urine samples with respective protein concentrations of 2, 5, 15, 30, 60, and 100 (mg/dl) was prepared by adding a protein to a urine, whose protein concentration $\approx 0$ (mg/dl). These respective urine samples and a urine whose protein concentration $\approx 0$ (mg/dl) were heated to be opacified. Each solution to be detected thus prepared was introduced into the sample cell 3 to measure the scattered light intensity, that is, the output signal from the photosensor 5 at this step.

Figure 5:
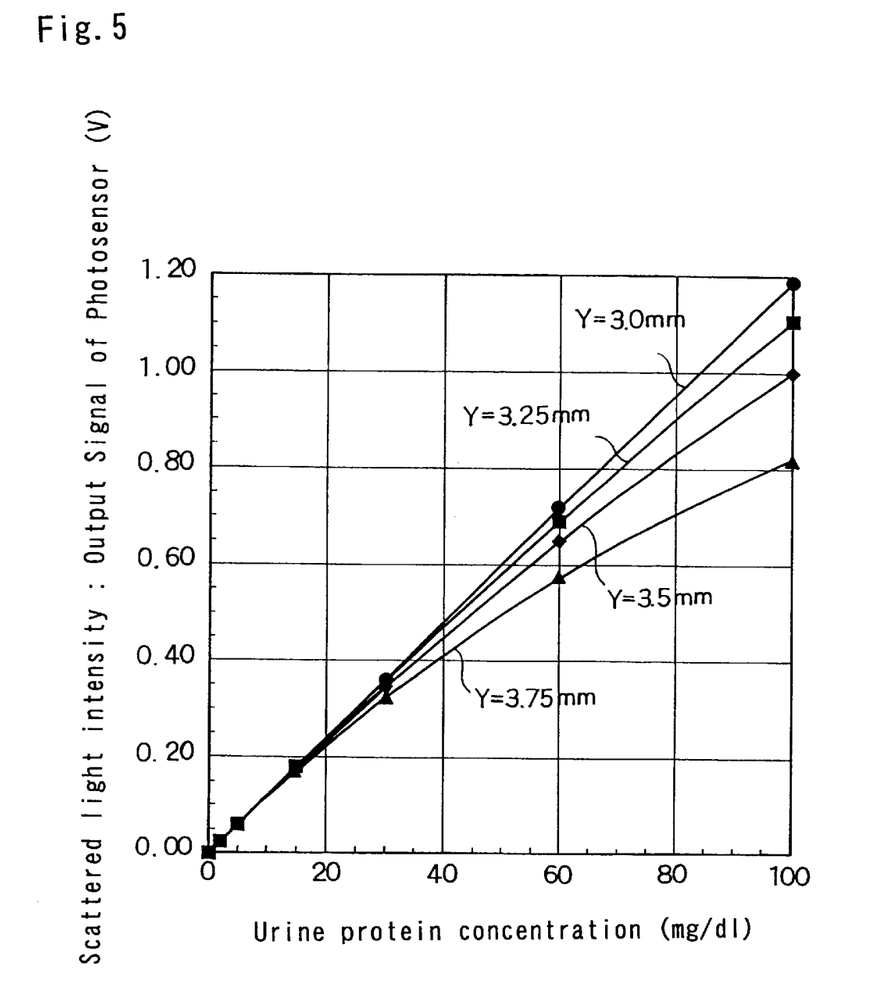
FIG. 5 is a graph showing the relation between the measured values of the scattered light intensity and the urine protein concentration in the embodiment of the present invention.

The results are shown in FIG. 5. In FIG. 5, the abscissa denotes the protein concentration, and the ordinate denotes the output signal (scattered light intensity) detected at the photosensor 5. FIG. 5 shows the results in the case where the distance Z was fixed at 2.0 mm, and the distance Y was changed into 3.0 mm, 3.25 mm, 3.5 mm, and 3,75 mm.

As apparent from FIG. 5, the shorter the distance Y is, the more excellent the linearity of the calibration curve showing the relation between the protein concentration and the scattered light intensity is. Further, the measured scattered light intensity is zero irrespective of the value of the distance Y when the protein concentration $\approx 0$ (mg/dl). This indicates that each measured value has not been affected by the scattered light arisen from the pollutants inside and on the surfaces of the optical window.

Figure 6:
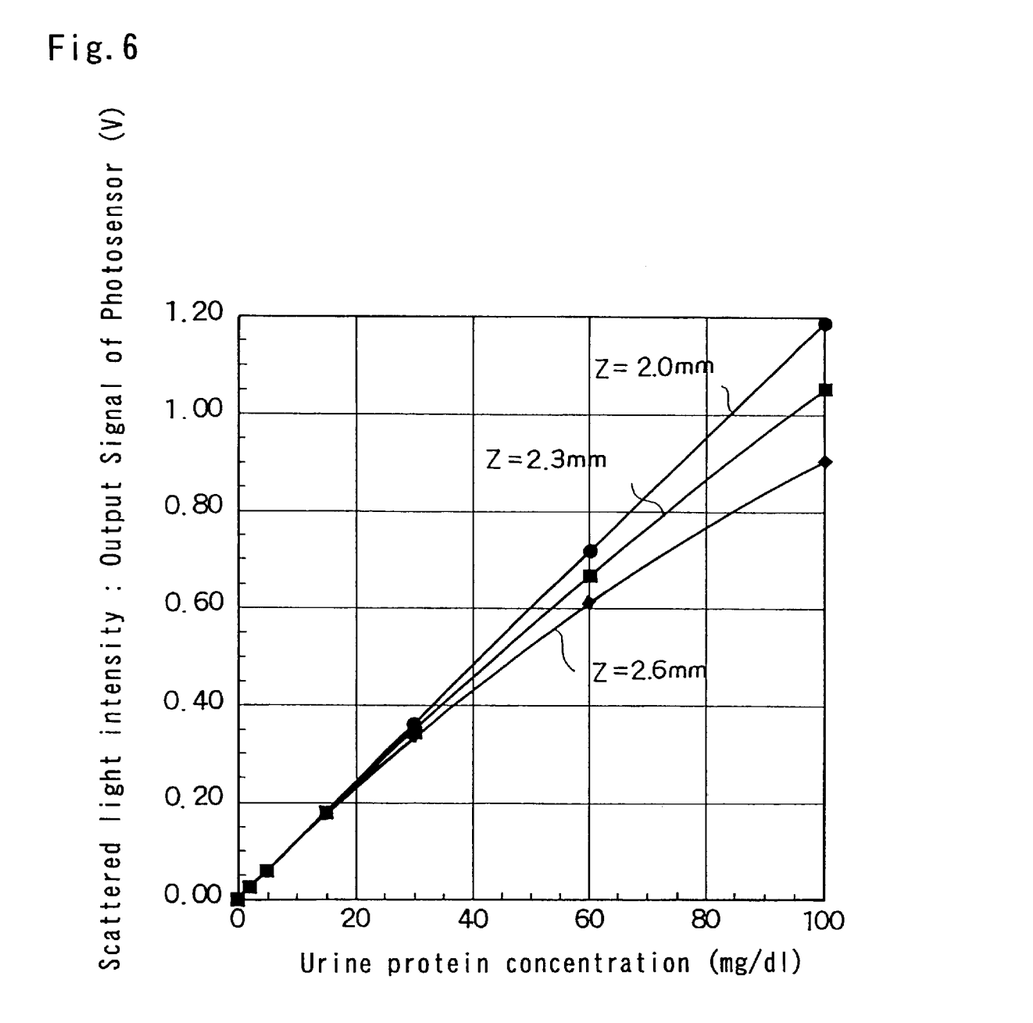
FIG. 6 is a graph showing the relationship between the measured values of the scattered light intensity and the urine protein concentration in another embodiment of the present invention.

Then, FIG. 6 shows the relation between the output signal (scattered light intensity) detected at the photosensor 5 and the protein concentration of the solution to be detected when measurement is carried out by changing the distance Z. This graph shows the results obtained by measuring the output signal from the photosensor 5 while changing the distance Z into 2.0 mm, 2.3 mm, and 2.6 mm.

As apparent from FIG. 6, the shorter the distance Z is, the more excellent the linearity of the calibration curve showing the relationship between the protein concentration and the scattered light intensity is. Further, the measured scattered intensity is zero irrespective of the value of the distance Z when the protein concentration $\approx 0$ (mg/dl). This indicates that each measured value has not been affected by the scattered light arisen from the pollutants inside and on the surfaces of the optical window.

As described above, by restricting the detecting angle of the photosensor, reducing the distance Y, and further reducing the distance Z so as to allowing the scattered light arisen from the solution to be detected in a region as close as possible to the first optical window for receiving the substantially parallel light to be incident upon the photosensor, the measurement of the scattered light intensity with an excellent linearity and a wide dynamic range could be implemented. Further, by previously confirming the position ($Y_{min}$ and $Z_{min}$) at which the influence of the scattered light arising from the optical window itself begins to occur with a liquid such as pure water, which does not generate a scattered light substantially, the accurate position (distances Y and Z) capable of removing the influence of the pollutants inside and on the surfaces of the optical window could be set. Namely, while the first optical window for receiving the light to be propagated through the inside of the solution to be detected, and the second optical window facing the photosensor are being contaminated, the position Y of the optical axis of the light to be propagated through the inside of the solution to be detected, and the position Z of the photosensor in the direction of the optical axis can be appropriately set so that the power of the scattered light incident upon the photosensor out of the scattered light arisen at both the optical windows is not more than a prescribed value.

Further, it was confirmed that, with these methods, the obstruction due to suspending particles such as bubbles and dust in the solution to be detected can also be eliminated other than removing the influence of the scattered light due to the optical window, so that a precise scattered light intensity reflecting the optical characteristics inherent in the solution to be detected can be measured.

Incidentally, although $Y_{min}$ and $Z_{min}$ were experimentally determined by using pure water, and the appropriate distances Y and Z were set from these values regarding the simplicity as important in this example, they can also be set in the following manner.

Namely, the refractive index of pure water at the wavelength (670 nm) of the substantially parallel light is about 1.331, while the refractive index of the urine, which is the solution to be detected, is about 1.333 to 1.344. The smaller the refractive index $n_s$ of the solution to be detected is, the larger the substantial detecting angle $2\theta_1$ is. Therefore, use of pure water results in that the values of $Y_{min}$ and $Z_{min}$ which are a little greater than in the case where the urine is used are determined. Therefore, by using a solution having the minimum refractive index (1.333) exhibited by the urine serving as the solution to be detected, it is possible to more exactly determine the values of $Y_{min}$ and $Z_{min}$ capable of inhibiting the obstruction by the scattered light arisen due to the pollutants inside and on the surfaces of the optical window.

Even if pure water is used as a simple procedure, there is no problem from the practical viewpoint. However, by setting the position Y of the optical axis of the light to be propagated through the inside of the solution to be detected, and the position Z of the photosensor in the direction of the optical axis so that the power of the scattered light measured by using a liquid having the minimum refractive index among solutions to be detected, and substantially generating no scattered light is not more than a prescribed value, it becomes possible to further improve the linearity, and other measured characteristics.

EXAMPLE 2

In this example, a urine opacified by mixing a reagent therein was used as the solution to be detected to measure the scattered light intensity corresponding to the turbidity thereof. Then, a calibration curve was formed based on the measured values to determine the protein concentration.

In Example 1 described above, there was carried out the method in which $Y_{min}$ and $Z_{min}$ were experimentally found by using the contaminated sample cell to set appropriate distances Y and Z from these values. In contrast, this example pertains to the method in which by defining a certain power level to such a degree that the scattered light arisen inside and on the surfaces of each optical window, and incident upon the photosensor 5 is substantially negligible and causes no problem from the practical viewpoint, appropriate distances Y and Z such as to satisfies the predetermined value are calculated from the minimum refractive index of the solution to be detected, and the power distribution of the substantially parallel light 2.

The substantially parallel light 2 is a Gaussian beam having a power density represented by the formula (1), and the power density is distributed to an infinite distance. Therefore, no matter how the distances X and Y are set, the power of the scattered light arisen inside and on the surfaces of each optical window, and incident upon the photosensor 5 cannot be made zero in principle. Further, since the influence of diffraction, if very minute, is added in Actuality, the diffracted component is also incident upon the photosensor 5.

However, from a practical viewpoint, the distances X and Y may be set at minimum in such A range that the power of the scattered light incident upon the photosensor 5 out of the scattered light arisen inside and on the surfaces of each optical window can be suppressed to a practically non-problematic level. For evaluating the practical influence of the scattered light arisen inside and on the surfaces of each optical window, which inhibits the measurement of the scattered light arising from the solution to be detected, r in the formula (1) is reexpressed as the formula (7):

$$r = k \times w_0 \qquad (7)$$

where k is a proportionality constant.

When k=1, the power present within the radius r accounts for 86.47% of the total power; when k=1.5, the power present within the radius r accounts for 98.89% of the total power; and when k=2, the power present within the radius r accounts for 99.97% of the total power. In other words, for example, when k=2, the power present outside the radius r accounts for only 0.03% of the total power.

It is the power of the substantially parallel light 2 propagating inside and on the surfaces of the second optical window facing the photosensor 5, that is, the power present outside the radius Y when r=Y in the formula (1) that determines the power of the scattered light arisen inside and on the surfaces of the second optical window facing the photosensor 5, and incident upon the photosensor 5.

Further, it is the power of the substantially parallel light 2, which generates the scattered light within the detecting angle of the shade column 6 in the first optical window, in other words, the power of the light propagating through a region that generates a scattered light receivable by the photosensor within the first optical window, to which the substantially parallel light is incident, that determines the power of the scattered light arisen inside and on the surfaces of the first optical window, which is for receiving the substantially parallel light 2, and incident upon the photosensor 5.

By setting the distances Y and Z in such a range that these powers can be suppressed to not more than a predetermined value which is almost negligible with respect to the total power of the substantially parallel light and practically allowable, it is possible to carry out the measurement with practically sufficient precision.

In this example, as the condition for achieving the value within the practically allowable range, the power of the substantially parallel light 2 propagating inside and on the surfaces of the second optical window facing the photosensor 5 was set to be 0.05% of the total power of the substantially parallel light 2. Further, the power of the substantially parallel light 2 in the region within the first optical window for receiving the substantially parallel light 2, which generates a scattered light within the detecting angle of the shade column 6, was set to be 1% of the total power of the substantially parallel light 2.

For satisfying these conditions, appropriate values of distances Y and Z were calculated and set in the following manner.

First, the distance Y was set. In accordance with the formulae (1) and (7), when $Y=r=2w_0$, the power present outside the radius r accounts for 0.03% of the total power. The power present closer to the optical window facing the photosensor than the optical axis was half, and 0.015% of the total power. A part thereof corresponds to the power of the substantially parallel light 2 propagating inside and on the surfaces of the second optical window facing the photosensor, thus satisfying the requirement of being not more than 0.05%, i.e., a predetermined value. Based on this, the distance Y was set as $k \times w_0 = 2 \times 1.5 = 3.0$ mm.

Then, a description will be given as to the setting of the distance Z by reference to FIG. 4. In FIG. 4, the point of intersection between a scattered light ray 8' propagating on the outermost side of the detecting angle restricted by the shade column 6, and the surface on the solution side of the first optical window for receiving the substantially parallel light 2 was referred to as C. The distance between the point of intersection C and the second optical window surface facing the photosensor was referred to as $Y_c$. Thus, the scattered light arisen at the first optical window located at the portion exceeding the $Y_c$ is present within the detecting angle. Herein, when k=1.5, the power present outside the radius r in case of $k \times w_0 = 1.5 \times 1.5 = 2.25$ mm accounted for about 1.11% of the total power. In FIG. 4, the power present on the righter side than the optical axis 4 (or 4'), that is, on the opposite side of the second optical window facing the photosensor out of the power outside the radius r accounted for 0.555% of the total power. A part thereof corresponds to the power of the substantially parallel light 2 in the optical window, which generates the scattered light within the detecting angle, thus sufficiently satisfying the requirement of being not more than 1%, i.e., the predetermined power value in the optical window.

Herein, from FIGS. 3 and 4, $Y_c$ can be expressed as the formula (9):

$$Y_c = (Z - (D/2 + t \times \sin \theta_2))/\tan \theta_1 \quad (9)$$

and the formula (8):

$$Y + k \times w_0 < Y_c \quad (8)$$

is required to be satisfied.

The refractive index of the urine as the solution to be detected at a wavelength of 760 nm falls within a range of from about 1.333 to 1.344. As described in Example 1. since the detecting angle becomes maximum when the refractive index is minimum, it was set that $n_s=1.333$. Further, the refractive index $n_g$ of the optical window of the sample cell 3 at this wavelength was about 1.514. From these refractive indices, the formulae (3), (4), and (5), $\theta_3 \approx 5.710°$, and $n_a \approx 1$, such results were given that $\sin \theta_2 \approx 0.0657$, and $\sin \theta_1 \approx 0.0746$. Using these numerals and formulae, and D=2 mm, and t=1 mm, from the formulae (8) and (9), the following formula (10) was obtained:

$$Y + 2.25 < (Z - 1.0657)/0.0748 \quad (10)$$

Substitution of Y=3 mm into the formula (10) yields 1.4584 mm<Z. Therefore, the distance Z was set at 1.5 mm.

Thus, the distances Z and Y were set to introduce a non-heated sample urine of the same type as used in Example 1 into the sample cell 3. Thereafter, a sulfosalicylic acid reagent (a reagent obtained by dissolving sodium sulfate in an aqueous solution of 2-hydroxy-5-sulfobenzoic acid) was mixed therein. Upon mixing the sulfosalicylic acid reagent, the protein component in the sample urine coagulated, resulting in a turbid solution to be detected. The relation between the scattered light intensity and the protein concentration measured for the solutions to be detected showed the same linear relation as the characteristics when Y=3.0 mm and Z=2.0 in FIGS. 5 and 6.

As described above, by restricting the detecting angle, and further minimizing the distance from the region generating the scattered light to the point from which the scattered light is emitted to the outside of the solution to be detected, it is possible to receive no influence of the scattered light arisen due to the pollutants adhering to the inside and/or onto the surface of the optical window, and reduce the probability of occurrence of obstruction due to suspending particles such as bubbles and dust.

Further, by minimizing the distance from the region generating the scattered light to the point from which the scattered light is emitted to the outside of the solution to be detected, it is possible to reduce the influence of the propagation loss during propagation of the scattered light through the inside of the solution to be detected. In this minimization, the threshold values of the distances X and Y receiving no influence of the scattered light arising due to the pollutants adhering to the inside and onto the surface of the optical window can be determined quantitatively in advance to set appropriate distances.

It is noted that, in each of the foregoing examples, the position Y of the optical axis of the light to be propagated through the inside of the solution to be detected, and/or the position Z of the photosensor in the direction of the optical axis were set under the condition that the detecting angle of the photosensor was constant so that the power of the scattered light arisen due to the pollutants inside the second optical window facing the photosensor and/or the first optical window for receiving the light to be propagated through the inside of the solution to be detected, and on the surfaces of the optical windows, and incident upon the photosensor, that is, a power resulting in a so-called noise was not more than a predetermined value. However, the detecting angle of the photosensor also ought to be set so that such power resulting in a noise is not more than a predetermined value.

Further, in the examples, the substantially parallel light 2 was a Gaussian beam. However, even when a beam having other power density distributions is used, the distances Y and Z can be set with the same method. Further, although a rectangular sample cell comprising transparent optical windows at four side walls was used as the sample cell, such a sample cell is also acceptable that at least two adjacent side walls are transparent. However, if the other two side walls not necessarily required are ground glass or the like, the scattered light arising here may obstruct the measurement. Accordingly, it is preferable that reflection and scattering prevention processing are performed.

As described above, with the method and apparatus for measuring a scattered light of the present invention, it is possible to carry out a high precision scattered light measurement from which the obstruction due to suspending particles such as bubbles and dust in the solution to be detected, the influence due to differences in refractive index and transmittance (turbidity), the influence of the scattered light arisen due to the pollutants adhering to the inside and the surface of the optical window, and the like have been eliminated to a practically satisfactory level. Further, since the influence of the propagation loss of the light to be propagated through the solution to be detected can be reduced, the measurable concentration range can be enlarged.

Still further, by applying the present invention, it is possible to carry out a urinalysis which is easy to maintain and control, has a wide measurable concentration range of protein, and has high reliability and practicability.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method for measuring a scattered light arising when a light is propagated through an inside of a solution to be detected, said method comprising the steps of:

allowing the light to be incident upon and propagated in said solution to be detected in a sample cell, which has at least a first optical window and a second optical window, from said first optical window; and measuring by a photosensor the scattered light propagating in a direction substantially perpendicular to the direction of said light propagating through the inside of said solution to be detected out of the scattered light arising in said solution to be detected from the second optical window, said scattered light output from the second optical window passes through an angle restricting means prior to reaching the photosensor, wherein a position Y of the optical axis of said light propagating through the inside of said solution to be detected is such that the power of the scattered light incident upon a photo detective area of said photosensor out of a scattered light arising inside and on the surfaces of said second optical window is not more than a predetermined value, said predetermined value being less than the minimum value of the power of the scattered light possessed by the solution to be detected when the solution to be detected has the lowest turbidity.

2. The method for measuring a scattered light in accordance with claim 1, wherein a surface of said second optical window closer to said solution to be detected is located substantially in parallel to an optical axis of said light propagating through the inside of said solution to be detected.

3. The method for measuring a scattered light in accordance with claim 1, wherein a position Z of said photosensor is set such that the power of a scattered light incident upon a photo detective area of said photosensor out of a scattered light arising from said first optical window is not more than a predetermined value within a practically allowable range.

4. The method for measuring a scattered light in accordance with claim 3, wherein the position Z of said photosensor is set such that a scattered light arisen in a region closest to the surface of said first optical window, said surface being closer to the solution to be detected, can be measured.

5. The method for measuring a scattered light in accordance with claim 3, wherein said predetermined value is set by defining the power of a scattered light arising inside and on the surfaces of the first optical window from a proportion of the power of the light propagating in a region within the first optical window, in which a scattered light receivable by the photosensor is generated, out of the power of the light to be propagated through the inside of the solution to be detected.

6. The method for measuring a scattered light in accordance with claim 1, wherein the position Y of said optical axis is set at a position closest to the surface of said second optical window, said surface being closer to the solution to be detected.

7. The method for measuring a scattered light in accordance with claim 1, wherein said light propagating through the inside of the solution to be detected is a linearly polarized light, and a scattered light propagating in a direction perpendicular to the polarization direction, which is a vibrating direction of a magnetic field of said light, is measured.

8. The method for measuring a scattered light in accordance with claim 1, wherein said light propagating through the inside of the solution to be detected is a substantially parallel light, and said light is made incident such that said light propagates in a direction perpendicular to the surface of the first optical window closer to said solution to be detected.

9. The method for measuring a scattered light in accordance with claim 1, wherein said predetermined value is set by defining the power of a scattered light arising inside and on the surfaces of said second optical window from a proportion of the power of the light propagating inside and on the surfaces of the second optical window out of the power of the light to be propagated through the inside of the solution to be detected.

10. The method for measuring a scattered light in accordance with claim 1, wherein said position Y of the optical axis and a position Z of the photosensor are set such that the power of a scattered light incident upon the photosensor out of the scattered light arisen at both the optical windows is not more than the predetermined value under the condition that said first and second optical windows are contaminated.

11. The method for measuring a scattered light in accordance with claim 10, wherein said position Y of the optical axis and said position Z of the photosensor are set such that the power of a scattered light to be measured by using a solution to be detected, which has a minimum refractive index and generates substantially no scattered light, is not more than the predetermined value.

12. A method of urinalysis comprising the steps of:

opacifying a urine as a solution to be detected by a process selected from the group consisting of heating and coagulating a protein therein, and mixing a reagent for coagulating the protein, measuring a scattered light arising in accordance with the opacity of said urine, and determining a protein concentration in said urine from a measured value, said measuring of scattered light comprising the steps of:
allowing a light to be incident upon and propagated in said solution to be detected in a sample cell, which has at least a first optical window and a second optical window, from said first optical window; and measuring by a photosensor the scattered light propagating in a direction substantially perpendicular to the direction of said light propagating through the inside of said solution to be detected out of the scattered light arising in said solution to be detected from the second optical window, said scattered light output from the second optical window passes through an angle restricting means prior to reaching the photosensor, wherein a position Y of the optical axis of said light propagating through the inside of said solution to be detected is such that the power of the scattered light incident upon a photo detective area of said photosensor out of a scattered light arising inside and on the surfaces of said second optical window is not more than a predetermined value, said predetermined value being less than the minimum value of the power of the scattered light possessed by the solution to be detected when the solution to be detected has the lowest turbidity.

13. A scattered light measuring apparatus, comprising: a rectangular sample cell having at least two adjacent transparent side walls each functioning as optical window and holding a solution to be detected; a light source for projecting a light into the solution to be detected in a direction perpendicular to the surface, which is in contact with the solution to be detected, of a first optical window of the sample cell in contact with the solution to be detected through the first optical window; a photosensor for detecting a scattered light arising when the light is propagated through the inside of the solution to be detected, and emitted through a second optical window adjacent to the first optical window; and a detecting angle restricting means for restricting the angle of a scattered light incident upon the photosensor within a predetermined angle centering on a direction perpendicular to the propagating direction of the light to be propagated through the inside of the solution to be detected, wherein a scattered light intensity of the solution to be detected is measured by an output signal from the photosensor.

* * * * *